(12) United States Patent
Girvan

(10) Patent No.: US 6,399,108 B1
(45) Date of Patent: Jun. 4, 2002

(54) COMPOSITIONS AND METHODS FOR THE TREATMENT OF SKIN DISORDERS

(75) Inventor: Don H. Girvan, St. Augustine, FL (US)

(73) Assignee: P.H.C., Inc., St. Augustine, FL (US)

( * ) Notice: Subject to any disclaimer, the term of this patent is extended or adjusted under 35 U.S.C. 154(b) by 0 days.

(21) Appl. No.: 09/607,266

(22) Filed: Jun. 30, 2000

Related U.S. Application Data

(60) Provisional application No. 60/141,668, filed on Jun. 30, 1999.

(51) Int. Cl.[7] .................... A61K 33/22; A61K 7/48; A61K 7/50; A61K 9/70; A61K 9/10
(52) U.S. Cl. ............... 424/659; 424/657; 424/658; 424/660; 424/402; 424/443; 424/445; 424/446; 424/447; 514/825; 514/826; 514/827; 514/828; 514/846; 514/847; 514/848; 514/858; 514/859; 514/860; 514/861; 514/862; 514/863; 514/864; 514/865; 514/871; 514/886; 514/887; 514/928
(58) Field of Search .................. 424/657–660, 424/402, 443, 445, 446, 447; 514/827, 828, 846, 847, 848, 859, 861–865, 886, 887, 928, 825, 826, 858, 860, 871

(56) References Cited

U.S. PATENT DOCUMENTS 4,911,925 A * 3/1990 Shatkina et al. ............ 424/401
5,021,185 A * 6/1991 Mustakallio ................ 510/158
5,244,679 A * 9/1993 Freston ........................ 424/659

FOREIGN PATENT DOCUMENTS

WO 00/47178 * 8/2000

OTHER PUBLICATIONS

Martindale The Extra Pharmacopoeia, The Phamaceutical Press, London, pp. 1343–1344, 1993.*

Chemical Abstracts 73: 7261, Abstracting NL 6,811,874, 1970.*

Cecil Textbook of Medicine, W.B. Saunders Co., Philadelphia, vol. 2, p. 2368, 1992.*

* cited by examiner

*Primary Examiner*—John Pak
(74) *Attorney, Agent, or Firm*—Kilpatrick Stockton LLP

(57) ABSTRACT

The present invention is directed to methods and compositions for treating skin disorders. The present invention is easily administered and can be used for both humans and animals. The compositions of the present invention comprise borate compounds and provide relief from skin disorder symptoms and lesions. Additionally, the present invention can be used to provide long term maintenance of symptom-free skin.

12 Claims, No Drawings

COMPOSITIONS AND METHODS FOR THE TREATMENT OF SKIN DISORDERS

This application claims the benefit of U.S. Provisonal application 60/141,668, filed on Jun. 30, 1999.

TECHNICAL FIELD

The present invention is directed to treatments for skin disorders. In particular, the invention is directed to compositions and methods for treatment of skin disorders by administering borate compositions.

BACKGROUND OF THE INVENTION

Skin disorders are debilitating to persons or animals who suffer with such a disorder. The disorders can range from the mildly irritating levels of discomfort to medically threatening conditions. The presence of skin lesions or associated inflammation may limit the lifestyle choices of the patient and limit the ability to work or maintain a particular lifestyle. Skin disorders are usually difficult to treat and often require long term efforts at controlling the lesions.

There is a long felt need for treatment of skin disorders. There are many treatments available, but they are expensive, hard to administer or have unwanted side effects. Additionally, these treatments are not successful, or only provide temporary relief for patients.

One example of such ineffective treatments for skin disorders is the treatment of psoriasis. Currently used topical treatments include topical steroids, coal tar compositions, anthralin, Vitamin D compositions, retinoid therapy, exposure to sunshine and other lotions and creams. Occlusion therapy, wrapping the lesions with coverings and medications, is also commonly tried. Common side effects from such treatments include skin thinning, stretch marks and resistance to medications. Coal tar treatments may make the skin more sensitive to UV rays and anthralin can irritate or burn skin surrounding the psoriatic lesions. Other topical treatments may cause allergic reactions or skin irritation, an unwanted effect in treating already irritated skin. Sun therapy may cause skin cancers that lead to more serious medical conditions and treatments. Patients may also try a variety of herbal or dietary remedies.

Phototherapy with UV B radiation is another treatment for skin disorders. It may be used alone or in conjunction with topical treatments. The side effects include skin cancer and skin aging. PUVA, a combined psoralen and UV A radiation treatment, has also been used to treat skin disorders. The patient usually takes psoralen by mouth and administers UV A radiation to the skin surface. The short term side effects include nausea, itching and redness of the skin. The long term effects include changes in the skin's pigmentation, premature aging of the skin and cataracts.

Some patients have severe skin disorders covering large areas of the skin and require spa-type treatments. For example, in treating widespread psoriasis, day treatment programs have been used. The patients spend six to eight hours every day for two to four weeks in the day treatment program. They are treated with tar, anthralin and UVB radiation. These special treatment centers are located in certain metropolitan areas and are not available to persons unable to travel and disrupt their lives to this extent. Additionally, there is no such treatment for animals that suffer from skin disorders.

Internal medications have also been used in treatment of skin disorders. Steroids have long been used, but have many side effects that limit the persons who can take the steroids and limit the amount of time steroids can be administered. Additionally, there are side effects from taking the steroids and from cessation of steroid medications once treatment ends. Other common medications include methotrexate and oral retinoids. Short term side effects from methotrexate treatment include nausea, fatigue, loss of appetite, and mouth sores. Long term use can lead to liver damage and patients taking methotrexate must be closely monitored for this damage. Oral retinoids pose particular problems for women who may become pregnant because retinoids cause birth defects in developing fetuses. Such teratogenic effects are serious risks for patients seeking skin disorder treatments. Additionally, women who may become pregnant cannot drink alcohol while taking retinoids because the metabolic products of the combination cause birth defects. Cyclosporine can also treat skin disorders, but it has the side effect of immune suppression, and is routinely given to prevent organ rejection in transplant patients.

What is needed are compositions and methods of treating skin disorders in humans and animals that do not have the serious side effects of current therapies. Additionally, what is needed are methods and compositions for treatment of skin diseases that are safe, easily administered and provide flexible enough treatment regimens for humans and animals. Furthermore, what is needed are compositions and methods of treating skin disorders that are safe for patients, easily handled, and safely stored, and that provide relief of symptoms and that can be used in long term maintenance care without creating additional medical problems for the user.

SUMMARY OF THE INVENTION

The present invention is directed to compositions and methods for treatment of skin disorders. In particular, the present invention is directed to skin treatments that comprise borate compounds. Such compositions and methods are safe and effective for humans and animals, and can provide short-term and long-term relief from such conditions.

A preferred embodiment of the present invention comprises administration, preferably topical administration, of compositions comprising borate compounds, in a sequential manner until the skin disorder is resolved or under control. Preferred compositions comprise borate compounds, preferably borate salts and most preferably, mixtures or admixtures of borate compounds and boric acid.

Accordingly, it is an object of the present invention to provide methods and compositions for the treatment of skin disorders.

It is another object of the present invention to provide methods and compositions comprising borate compounds or borate compounds admixed or mixed with boric acid.

Further objects of the present invention comprise methods and compositions that are easily administered for short term relief of skin disorders.

Another object of the present invention comprises methods of topical administration of compositions for the treatment of skin disorders.

Yet another object of present invention comprises compositions of borate compounds that are administered for treatment of skin disorders.

An additional object of the present invention comprises methods and compositions for treatment of skin disorders that can be used for long-term treatment of skin disorders.

A further object of the present invention comprises methods and compositions that can be used for short term treatment of skin disorders.

DETAILED DESCRIPTION

The present invention is directed to methods and compositions for treatment of skin diseases. Such skin diseases include, but are not limited to, dermatological conditions linked to disorders of keratinization involving differentiation and proliferation, in particular, acne vulgaris, comedonic or polymorphic acne, nodulocystic acne, acne conglobata, senile acne and secondary acnes such as solar, drug or occupational acne; for other types of keratinization disorders especially ichthyoses, ichthyosiform conditions, Darier's disease, palmoplantar keratoderma, leukoplakia and luecoplakiform conditions or lichen and lichen planus; dermatological disorders having an inflammatory or immunoallergic component, in particular, all forms of psoriases, either cutaneous, mucosal or ungual, and psoriatic rheumatism, and cutaneous atopy such as eczema or respiratory atopy, dry skin, inflammation of the skin, solar erythema, skin allergies or other skin disorders of the epidermis and dermis. The present invention contemplates the treatment of skin disorders of humans and animals.

The present invention comprises compositions of borate compounds. In particular, preferred embodiments of the compositions comprise mixtures or admixtures of borate compounds and boric acid. The compositions may also comprise borate compounds. Preferably, the borate compound is a borate salt. The borate salt in a preferred composition is preferably an alkaline metal tetraborate pentahydrate or an alkaline metal tetraborate decahydrate. The present invention contemplates use of any hydration state of the salt.

The alkaline metal can be any alkaline metal that is compatible with the borate ion. Such alkaline metals include, but are not limited to, sodium, potassium, and lithium. A preferred composition that can be used in the methods of the present invention comprise a borate compound mixed or admixed with boric acid. The combination of borate salt and the boric acid can be in the range of a ratio of 5 to 95 borate compound to 95 to 5 boric acid by weight. In the composition for use in the methods of the present invention, the composition preferably comprises a range of between approximately 30% to 90% borate compound and 70% to 10% boric acid, more preferably, 40% to 80% borate compound and 60% to 20% boric acid, most preferably, 50% to 70% borate compound and 50% to 30% boric acid. A most preferred composition comprises a mixture of approximately 70% borate compound, preferably, sodium tetraborate and approximately 30% boric acid, by weight. A most preferred composition comprises essentially arsenic-free borate compounds.

The composition may further contain fillers, solvents, fragrances or other carriers, modifiers or enhancements. A preferred additive is an organically based fragrance, particularly an organic fragrance in a concentration between 0.01 and 0.5% by weight of the total composition, containing ethanol, 2-(2-ethoxyethoxy)-octanal, 2-(phenylmethylene)-1,6-octadien, -3-ol, 3,7-dimethyl-2,6, octadien-1-ol, 3,7-dimethyl-, (E) benzeneethanol.

The methods of treatment of the present invention comprise addition of the compositions of the present invention to water or other solvents to form a solution. That solution is then applied to the patient's skin. The compositions of the present invention may be added in almost any concentration that allows for the compositions to go into solution, or be dissolved in the solvent. Another embodiment of the compositions is to form a thickened paste or gel-like composition that can be applied to the skin, depending on the site of skin disorder and the type of skin disorder. Other methods of administration include creams and lotions for the application of the borate compositions to the skin. Such lotion and cream formulations are known to those skilled in the art.

The formulations of the present invention that are topically applied, such as gels, creams, or lotions, may also contain other compounds or ingredients that may be beneficial to the skin such as topical pharmaceuticals, including but not limited to antibiotics, antihelminthics and antifungal compounds; herbs; infusions; vitamins; dietary aids; and minerals. Such additional compounds may also be added to the compositions of the present invention that are dissolved in bodies of water or other solvents. These gel, paste, cream and lotion formulations comprise similar ratios of borate salt to boric acid. Such ratios comprise 50–90 borate salt to 50 to 10 boric acid.

For the compositions that comprise adding a dry composition to a solvent to form a solution, preferred concentrations are to add from 4 to 50 ounces of a preferred composition to a body of water large enough to soak the skin of the subject. Another approximate range in concentration may be from 50 to 500 ppm of borate. For paste, gel, cream or lotion applications, the concentrations of the compositions may be higher and can easily be determined by their effectiveness in treating the particular skin malady. These compositions are determined, in part, by the consistency of the final product. A range of 20 ppm to 500 ppm of borate can be used in such compositions, preferably 50 ppm to 300, more preferably 50 ppm to 250, most preferably 50 to 200.

An additional method of treating skin conditions comprises soaking cloths or bandages in a solution of the compositions of the present invention and applying the cloths or bandages to the skin site. Such solutions may comprise a range of approximately 50 to 500 ppm of borate for less severe skin conditions, or may comprise 50 ppm to 15,000 ppm for other skin conditions. Such cloths or bandages can be made from any material that can contain a borate solution and then provide it to a skin site. Preferably, the cloth or bandage would also maintain a moist environment for the skin site. Reservoir-type patches could also be used to maintain the compositions of the present invention at a particular site on the skin. These methods and compositions are particularly effective in the treatment of animals with skin conditions because the application of patches, bandages or cloths allows for movement of the animal and thus, prevents having to restrain the animal to soak its skin. Such methods are also effective for a human, who can treat a small effected area of skin with such a method of application without interfering with the human's regular activities.

The methods of treatment of the present invention comprise administration of the compositions to the skin of the subject with the skin disorder. The administration may be from 1 to 20 times daily until relief in symptoms is achieved. The administration may also be constant, such use of a patch or bandage. The frequency of administrations may vary for individual subjects. A preferred method of administration is application to the skin site of a preferred composition at least once a day, preferably, two time daily, and more preferably three times daily in a solution. Another preferred method of administration comprises wearing a dressing applied directly to the skin site comprising a preferred composition, wherein the dressing is worn for 10–24 hours, and a fresh dressing is worn until the skin condition is alleviated.

The compositions of the present invention may be administered by placing the subject's entire body in a pool, spa, bathtub or similar container, by encasing the afflicted skin only in a container with the compositions of the present invention or application of the compositions directly to the skin such as in a paste, gel, cream or lotion composition or solutions of the compositions soaked into dressings, cloths or patches that are then applied to the skin of the subject.

The compositions of the present invention are not harmful to the external surfaces of humans or animals and thus, varying concentrations of compositions of the present invention can be used on one or many individuals. An individual may begin administration of a low concentration solution of a composition comprising sodium tetraborate and boric acid, for example aprroximately 70:30 borate salt to boric acid composition, in water of approximately 50 ppm. The concentration may be increased, to 300 to 500 ppm, until the skin disorder clears. Another embodiment of the present invention comprises administration of higher concentrations of the compositions, such as a 500 ppm solution of borate salt/boric acid mixture, until clearance of the skin disorder and then maintenance of the clear condition by continuous administration of lower concentrations of the same composition.

A cream, lotion, gel or paste composition can be applied to the skin site and worn continuously. Such compositions may comprise 50–70 percent sodium tetraborate and 20–50 percent boric acid, and be at a concentration of 50 to 15,000 ppm of borate. Cloths or bandages containing such solutions may also be applied 2–20 times daily to the skin site. Compositions may be sprayed on the surface, for example, using an atomizing sprayer.

The frequency of administration of the compositions of the present invention may be much higher in the earlier treatment schedule and can taper to maintenance levels. For example, a subject might bathe 1 or 5 times daily in a preferred composition for the first two weeks of treatment and then change to bathing twice daily for two weeks, followed by once daily bathing in a preferred composition.

The present invention contemplates combinations and variations of these and other administration methods and routes. For example, there may be multiple daily administrations of differing concentrations of the compositions, or single daily administrations of differing concentration of the compositions. It is well known to those skilled in the art to apply differing administration routes and schedules to achieve relief of symptoms.

The methods of administration comprise methods that address such issues as the type of skin disorder the subject has, the extent or severity of the disorder, the past medical history of the subject, the lifestyle and availability for treatment, the age, gender and species, and the specific locations of the lesions and the differences in skin types.

The present invention offers many advantages over current treatments for skin diseases and disorders. The compositions and methods of the present invention are easy to administer and do not cause any harm to the skin surface or external features of the subject. These treatments are not difficult to administer, are not messy and do not cause unwanted side effects from accidental exposure to external structures. Treatment can be continued indefinitely without creating undue side effects or cumulative effects in the subjects or in the application devices or care givers. The compositions of the present invention are relatively inexpensive and can be administered by almost any person without any special devices or training. Furthermore, the compositions are not harmful to humans or animals, are not carcinogenic and are safe to store and ship.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

One example of treatment of skin disorders was a 75 year old male who suffered from psoriasis for 30 years and had inflammation, patches of thickened skin, cracked skin at elbows, knees, palms, feet, and silvery scales that were more prevalent in winter.

Treatment was begun using a mixture of 70% sodium tetraborate pentahydrate and boric acid 29.5% to 29.9% and an organic fragrance between 0.01 and 0.5% containing ethanol, 2-(2-ethoxyethoxy)-octanal, 2-(phenylethylene)-1, 6-octadien, -3-0L, 3,7-dimethyl-2,6, octadien-1-0L, 3,7-dimethyl-, (E) benzene ethanol.

The subject placed 8 ounces of this powder mixture in a stream of hot water entering his bath tub and then added cooler water after the powder dissolved. The subject then soaked his entire body in the tub for one and one-half hours every other day. Following three treatments, his sores began healing, pain disappeared and red inflammation diminished by 50%. Between the third and fourth week of treatment, the subject recovered from his symptoms. Treatment was then changed to a one and one-half hour soak every third day and the symptoms did not return.

The subject suspended treatment and symptoms began to recur during the fourth week without treatment. Treatment was resumed every other day and the subject began developing clear skin within one week. Treatment continued at this administration schedule and the subject has normal skin condition without any psoriasis symptoms.

Example 2

Another subject was an elderly woman, age 86. The subject had sores, scale and redness on 60% of her body. She experienced constant pain and had trouble sleeping. The subject used a 50–100 ppm solution of a composition comprising 70% sodium tetraborate and approximately 29% boric acid, in a full body bath, every other day for 1–2 hours.

During the first ten days of treatment, the subject noticed that the itching and burning went away and she was able to sleep at night without discomfort. Following twenty-three days of treatment, soaking one and one-half hours every other day, for a total of eleven times, the subject's sores healed, and the red inflamed skin was gone.

Example 3

Thirty patients were treated with the composition of Example 1 and all have recovered from their skin disorder symptoms. Prior to this treatment, all of these patients had received the treatments listed by the National Psoriasis Foundation and yet continued suffering from psoriasis. Patients soaked in bathtubs and spas similar to the schedule of Example 2.

It should be understood, of course, that the foregoing relates only to preferred embodiments of the present inven-

What is claimed is:

1. A method of treating skin disorders, comprising, topically administering an effective amount of a composition consisting essentially of a borate salt and boric acid, wherein the skin disorder is selected from the group consisting of ichthyoses; ichthyosiform conditions; lichen; lichen planus; all forms of psoriases; cutaneous rheumatism; mucosal rheumatism; ungula rheumatism; psoriatic rheumatism; cutaneous atopy; eczema; respiratory atopy; dry skin; inflammation of the skin; skin allergies; and combinations thereof.

2. The method of claim 1, wherein the composition is administered every other day.

3. The method of claim 1, wherein the composition consists essentially of a ratio of 50% to 90%, by weight, of borate salt and 50% to 10%, by weight, of boric acid.

4. The method of claim 1, wherein the composition consists essentially of from about 20 ppm to about 15,000 ppm of the borate salt and boric acid.

5. The method of claim 4, wherein the composition consists essentially of from about 50 ppm to about 500 ppm of the borate salt and boric acid.

6. The method of claim 1, wherein the composition is administered using a cloth or bandage that includes the composition and is applied to the skin to be treated.

7. The method of claim 6, wherein the composition consists essentially of from about 20 ppm to about 15,000 ppm of the borate salt and boric acid.

8. The method of claim 6, wherein the composition consists essentially of from about 50 ppm to about 500 ppm of the borate salt and boric acid.

9. The method of claim 1, wherein the composition is administered by placing the skin to be treated in a pool, spa, bathtub or similar container and touching the skin to be treated with a solution including the composition.

10. The method of claim 9, wherein the composition consists essentially of from about 50 ppm to about 500 ppm of the borate salt and boric acid.

11. The method of claim 1, wherein the composition is administered by including the composition in a carrier selected from the group consisting of cream, lotion, gel and paste and applying the carrier to the skin to be treated.

12. The method of claim 11, wherein the compositions consists essentially of from about 20 ppm to about 15,000 ppm of the borate salt and boric acid.

* * * * *